United States Patent [19]
Ishida et al.

[11] Patent Number: 5,632,906
[45] Date of Patent: May 27, 1997

[54] APPARATUS AND METHOD FOR TRANSFERRING SEPARATED COMPONENT IN LIQUID FROM A FLEXIBLE BAG IN A CENTRIFUGAL CONTAINER

[75] Inventors: Noboru Ishida, Shizuoka-ken; Atsuo Nakamura, deceased, late of Kyoto, by Yoshiko Nakamura, Tomoyo Nakamura, legal representatives; Norio Hosono, Shizuoka-ken, all of Japan

[73] Assignee: Terumo Kabushiki Kaisha, Tokyo, Japan

[21] Appl. No.: 83,297

[22] Filed: Jun. 29, 1993

[30] Foreign Application Priority Data

Jun. 30, 1992 [JP] Japan .................... 4-197898

[51] Int. Cl.$^6$ .................... B01D 21/26; B65D 35/28
[52] U.S. Cl. .................... 210/787; 210/109; 210/209; 210/416.1; 210/767; 210/782; 222/214; 604/408
[58] Field of Search .................... 210/767, 782, 210/787, 789, 109, 515, 516, 523, 929, 416.1, 86, 94, 97; 222/92, 94, 95, 103, 209, 249, 214, 386.5, 105; 604/141, 142, 143, 146, 147, 133, 181, 183, 185, 408, 410

[56] References Cited

U.S. PATENT DOCUMENTS

| | | | |
|---|---|---|---|
| 1,872,837 | 8/1932 | Smith | 222/102 |
| 3,151,616 | 10/1964 | Selfon | 222/102 |
| 4,303,193 | 12/1981 | Latham, Jr. | |
| 4,322,298 | 3/1982 | Persidsky | 210/787 |
| 4,439,177 | 3/1984 | Conway | 494/45 |
| 4,447,220 | 5/1984 | Eberle | 494/26 |
| 4,466,888 | 8/1984 | Verkaart | 210/232 |
| 4,539,005 | 9/1985 | Greenblatt | 604/141 |
| 4,663,032 | 5/1987 | Loos et al. | 210/97 |
| 4,976,851 | 12/1990 | Tanokura et al. | 210/94 |
| 5,045,185 | 9/1991 | Ohnaka et al. | 210/94 |
| 5,135,646 | 8/1992 | Tanokura et al. | 210/94 |

FOREIGN PATENT DOCUMENTS

WO00145  1/1992  WIPO .

*Primary Examiner*—John Kim
*Attorney, Agent, or Firm*—Burns, Doane, Swecker & Mathis, LLP

[57] ABSTRACT

An apparatus and method for transferring a centrifugally separated component in a liquid contained in a flexible bag is disclosed. The apparatus is composed of a centrifugal container for accommodating flexible blood collecting bag filled with blood, and a pushing mechanism for pushing the blood collecting bag. The pushing mechanism is composed of a pair of rollers for pushing a soft material part of the cylindrical portion of the centrifugal container from opposite directions in such a manner that the soft material part is deformed inwardly to project inside the centrifugal container and increase inner pressure of the flexible bag to transfer separated component out of the flexible bag. According to the apparatus and method, the yield for collecting the separated component obtained by centrifugal separation can be increased, and the time required for collection can be decreased.

8 Claims, 8 Drawing Sheets

APPARATUS AND METHOD FOR TRANSFERRING SEPARATED COMPONENT IN LIQUID FROM A FLEXIBLE BAG IN A CENTRIFUGAL CONTAINER

BACKGROUND OF THE INVENTION

1. Field of the Invention

This invention relates generally to apparatus and method for transferring a separated component in a liquid, and more particularly to apparatus and method for transferring or taking out a centrifugally separated component in a liquid such as blood contained in a blood bag.

2. Description of the Prior Art

In carrying out blood transfusion, recently, blood collected from a donor is centrifuged with a centrifugal separator for separating the collected blood into blood components, and then only the component required for a patient is transfused, in order to utilize the blood effectively and to reduce a burden on the patient who receives a blood transfusion. Owing to this component transfusion, it has become possible to utilize blood more effectively, as compared with the whole blood transfusion so far adopted.

In the above-mentioned component transfusion, connected bags (referred to as "multiple bag system") composed of a blood collecting bag and one or more bags are used.

As one of the multiple bag systems, there is known a triple bag system, which comprises a blood collecting bag, a platelet concentrate preserving bag (hereinafter, referred to as "PC bag") and a plasma preserving bag (hereinafter, referred to as "plasma bag") which are connected to each other through tubes. The blood collected into the blood collecting bag is centrifuged at least once to separate the blood into three components of erythrocyte concentrate, platelet concentrate, and platelet-poor plasma (hereinafter, referred to as "PRP method"), and the separated components are preserved in the blood bag, the PC bag and the plasma bag, respectively.

In the multiple blood bag system as described above, the respective bag is formed by laminating flexible polyvinyl chloride sheets and further fusing the periphery thereof. The reasons why the flexible polyvinyl chloride is used is that this material has an appropriate gas penetrability, and further that this material is excellent in preservation of cells such as erythrocyte, platelet. etc., in heat-resistance in autoclave sterilization, and in flexibility endurable to centrifugal separation and suitable for shake preservation. Further, the material is also low in manufacturing cost.

The blood collected into a blood collecting bag is centrifuged by placing the blood collecting bag in a centrifugal cup formed of a hard material and formed into a cup-shaped container and mounting the centrifugal cup with the blood collecting bag to a centrifugal separator. Further, the separated components are collected in accordance with the following steps, that is, first the blood collecting bag is removed from the centrifugal cup; the blood collecting bag is then set to an automatic separating stand; and thereafter the blood collecting bag is pressed, so that the supernatant plasma layer is discharged. As the automatic separating stand, for example, one disclosed in U.S. Pat. No. 4,976,851 can be used.

In the method as described above, however, after the centrifugal separation, the following operations are required, that is, the blood collecting bag is removed from the centrifugal cup, the removed bag is then transferred to the separating stand, and thereafter the bag is set to the separating stand. Therefore, there are various problems in that the blood collecting bag is shaken or vibrated during the above-mentioned operations and further the bag is likely to be deformed because of its flexibility. With this result, the interfaces between the respective two layers of the three separated components are likely to be disturbed during the operations, thus leading to the problem that yield (quantity of collection or purity) of each of the separated components is deteriorated. When the yield of each of the separated components is lowered as described above, the quality of blood products is also degraded, and therefore there exists such a case that the blood collecting bag must be centrifuged again as occasion demands.

In addition, since it takes a long time to take out the blood collecting bag from the centrifugal cup and further to set the bag to the separating stand. In particular, if these operations are carried out carefully so as not to disturb the interfaces between the respective separated components, a further long time is required.

SUMMARY OF THE INVENTION

The object of the present invention is to provide apparatus and method which can transfer a centrifugally separated component in a liquid contained in a flexible bag with improved yield for each separated component.

The other object of the present invention is to provide apparatus and method which can collect the centrifugally separated component from the liquid with high yield, without removing out the flexible bag in which the liquid is contained from the centrifugal cup.

In order to achieve the above-mentioned objects, the present invention is directed to an apparatus for transferring a separated component in a liquid contained in a flexible bag in airtight condition after centrifuging the flexible bag. The apparatus includes a centrifugal container for accommodating the flexible bag therein, and the container is adapted to be removably attached to a centrifugal separator. The apparatus further includes pressing means for pressing the flexible bag accommodated in the centrifugal container to increase an inner pressure of said bag while the bag is released from the airtight condition, so that a predetermined separated component can be discharged from the bag.

Further, the present invention is also directed to a method of transferring a centrifugally separated component in a liquid contained in a flexible bag under airtight condition after centrifuging the flexible bag. The method is carried out by accommodating a flexible bag in which the liquid Is contained under the airtight condition into a centrifugal container which is removably attached to a centrifugal separator; centrifuging the flexible bag accommodated in the centrifugal container by the centrifugal separator to separate the liquid in the flexible bag into predetermined components thereof; and pressing the flexible bag under the condition that the flexible bag is accommodated in the centrifugal container to increase inner pressure of the bag while the bag is released from the airtight condition, to take out the predetermined separated component in the liquid from the flexible bag.

When the apparatus and method as described above are adopted to transfer separated blood components, the following processes are taken place.

Any required amount of blood is collected into a flexible blood collecting bag. This bag is placed in the centrifugal container, and then the container in which the bag is accommodated is set to the centrifugal separator for centrifugal separation. The blood in the blood collecting bag is separated by the centrifugal separation into three layers of plasma layer, buffy coat layer, and erythrocyte layer.

After the centrifugal separation, the centrifugal container is removed from the centrifugal separator, and thereafter the removed cup is fixed to a separating stand, for instance. Then, the blood collecting bag accommodated in the centrifugal container is pressed by actuating the pressing means. Since the inner pressure of the blood collecting bag increases, the upper plasma layer is discharged through a tube connected to the blood collecting bag, so that the plasma can be transferred to another bag or the like and collected therein.

In this case, since the plasma is transferred and collected, after centrifugal separation, without removing the blood collecting bag from the centrifugal container and further without setting the blood collecting bag to a separating stand, the time and labor required for the operation can be reduced. Further, the disturbance at the respective interfaces between two of the three separated component layers will not occur due to vibration or bag deformation which are likely to be caused when the blood collecting bag is removed, transferred or hanged. In addition, the yield of the collected plasma can be improved.

Further, in the present invention, since the upper plasma layer is raised and then discharged under the condition that the inner pressure of the blood collecting bag is kept increased and further the respective interfaces between the layers is kept stationary, It is possible to avoid that the other component in the lower layer below the plasma layer is mixed with the plasma, thereby enabling one to increase the yield for the plasma. In addition, when the separated buffy coat layer is transferred and further collected, the yield therefore can be also improved in the same way as with the case of the plasma collection. In this regard, it should be noted that the liquid to be contained in the flexible bag is not limited to blood. Bone marrow fluid can be used instead of blood.

Preferably, the pressing means is includes an expandable and contractible cuff disposed between the inner surface of the centrifugal container and the outer surface of the flexible bag, and a fluid supplying means for supplying a working fluid into said cuff to expand it.

Alternatively, the pressing means may include a pressing member to be inserted into said centrifugal container through the opening formed in the container, for pressing the flexible bag, and driving means for driving the pressing member.

Alternatively, the pressing means may include a pushing member for pushing a soft material part of the centrifugal container in such a manner that the soft material part is deformed inwardly to project inside the container, and driving means for driving the pushing member.

Alternatively, the pressing means may include a mechanism for fixing one end of the flexible bag, and rotating means for rotating the other end of the flexible bag to twist the bag.

Alternatively, the pressing means may include a fastening member for fastening the outer surface of the flexible bag.

Alternatively, the pressing means includes a mechanism for reducing the size of the flexible bag accommodated in the container.

Further, in the apparatus and method according to the present invention, it is possible to use sucking means for sucking the separated component in the bag in addition to the pressing means. If the sucking means is provided in addition to the pressing means, it becomes possible to maintain high yield which is the same rate as that where the pressing means is used alone and shorten the time required for collecting the separated component.

Other objects, structures and advantages of the present invention will become apparent from the following descriptions of the preferred embodiments when taken in conjunction with the accompanying drawings.

DETAILED DESCRIPTION OF THE PREFERRED EMBODIMENTS

An apparatus and a method for transferring a separated component in a liquid according to the present invention will be described in detail hereinbelow with reference to the attached drawings.

Figure 1:
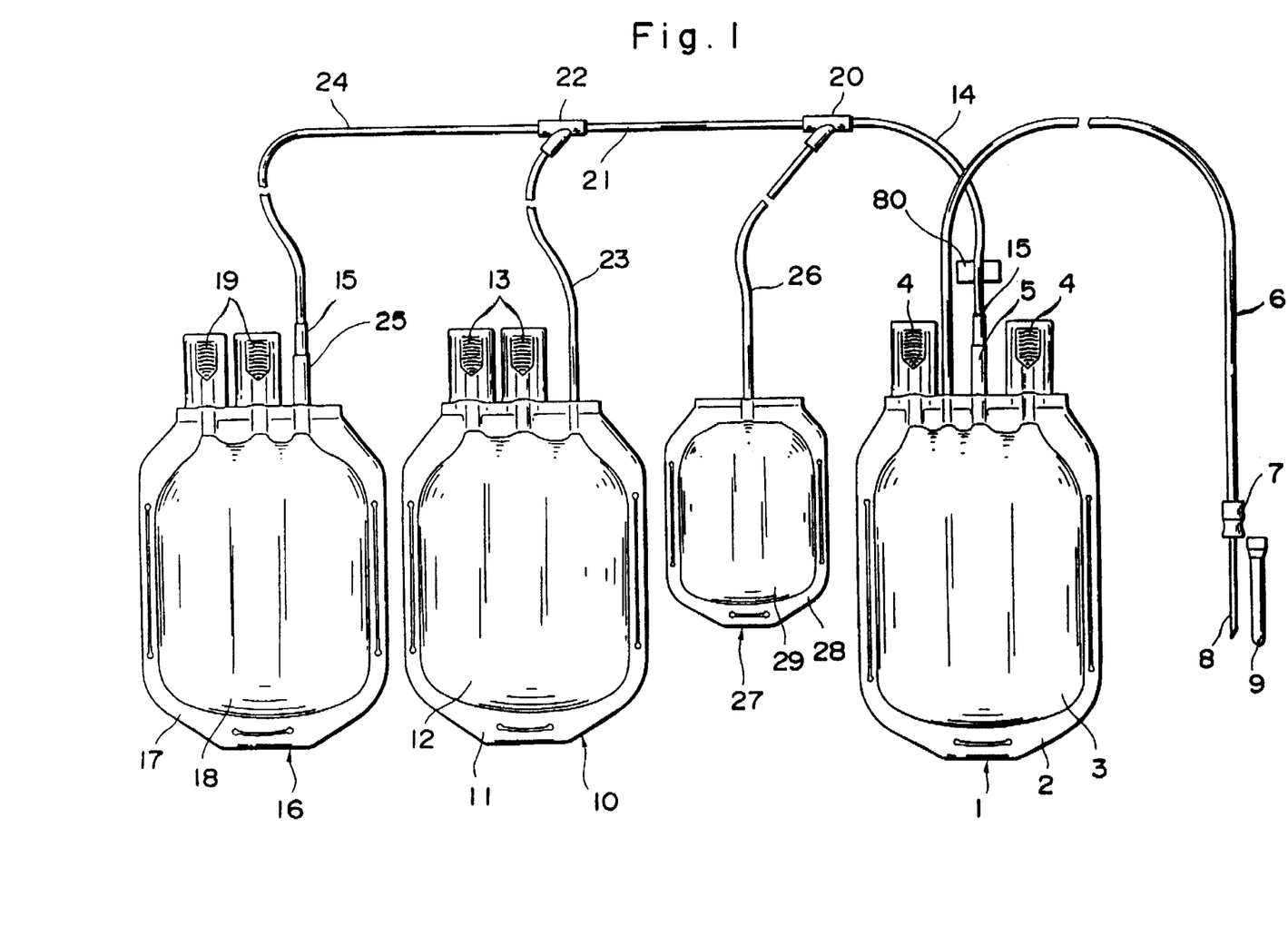
FIG. 1 is a plan view showing an example of the connected bags to which the present invention is applied.

First, the typical multiple bag system used for the apparatus according to the present invention will be explained. FIG. 1 is a plan view showing an example of the multiple bag system. The multiple bag system shown in FIG. 1 is constituted as quadruple (four-connection) bags which are composed of a blood collecting bag, a PC bag, a plasma bag, and a sub-bag (buffy coat bag).

The blood collecting bag 1 shown on the right side in FIG. 1 is formed into a closed bag by laminating flexible sheets of a resin material such as soft polyvinyl chloride and further fusing a peripheral sealing portion 2 thereof in accordance with fusing method (e.g., thermal fusion, high frequency fusion, etc.) or bonding the portion 2. In the space defined by the two sheets and enclosed by the sealing portion 2, there is formed a blood component accommodating section 3 to which collected blood or erythrocyte concentrate obtained by centrifuging the blood is to be contained.

In the upper portion of the blood collecting bag 1, there is formed two opening portions 4 provided with a peeling tub, respectively. Further, a blood outlet 5 is formed between the two opening portions 4 so as to be connected to another bag. One end of a tube 14 is connected to this outlet 5 via a connecting member 15.

Further, a bifurcated connector 20 is connected to the other end of the tube 14. Another tube 21 is connected to this bifurcated connector 20. Further, another bifurcated connector 22 is connected to the other end of this tube 21.

Further, it is preferable to constitute the connecting member 15 so as to provide with a path closing member (not shown) inside thereof. The path closing member is adapted to be broken by bending the connecting member 15 to allow fluid communication in the connecting member 15. Accordingly, the closing member functions in such a way that fluid communication in the connecting member 15 is kept impossible before broken, but the fluid communication therein becomes allowed after broken. As such a closing member, it is possible to use a Click Chip which is a product name of TERUMO Kabushiki Kaisha, for instance. In this invention, alternatively, it is possible not to provide the connecting member 15 as described above. In this case, it is preferable to close or open the tube 14 appropriately with the use of a clamp.

Further, one end of a flexible tube 6 communicating with the blood component accommodating section 3 is connected to the upper portion of the blood collecting bag 1. To the other end of this tube 6, a blood collecting needle 8 is attached via a hub 7. Further, there is provided a cap 9 which is attached to the hub 7 to cover the needle 8.

The plasma bag 10 shown at the second position from the left side in FIG. 1 is also formed into a closed bag by laminating flexible sheets of a resin material such as soft polyvinyl chloride and further bonding a peripheral sealing portion 11 thereof in accordance with fusing method (e.g., thermal fusion, high frequency fusion, etc.). In the space defined by the sheets and enclosed by the sealing portion 11, a plasma accommodating section 12 is formed to accommodate plasma (platelet-poor plasma, in particular) separated from the blood in the blood collecting bag 1.

In the upper portion of the plasma bag 10, there are formed two opening portions 13 provided with a peeling tub, respectively.

Further, one end of a flexible tube 23 communicating with the plasma accommodating section 12 is connected to the side of the opening portion 13 of the upper portion of the bag 10. The other end of this tube 23 is connected to the bifurcated end of the bifurcated connector 21. Therefore, the blood component accommodating portion 3 of the blood collecting bag 1 communicates with the plasma accommodating portion 12 of the plasma bag 10 through the tubes 14, 21 and 23 and the bifurcated connectors 20 and 22.

The PC bag 16 shown on the left side in FIG. 1 is also formed into a closed bag by laminating flexible sheets of resins such as soft polyvinyl chloride and further bonding a peripheral sealing portion 17 thereof in accordance with fusing method (e.g., thermal fusion, high frequency fusion, etc.). In the space defined by the sheets and enclosed by the sealing portion 17, a platelet accommodating section 18 is formed to accommodate platelet (platelet concentrate plasma) obtained by centrifuging the blood.

In the upper portion of the blood PC bag 16, there are formed two opening portions 19 which are provided with a peeling tub, respectively. Further, an outlet 25 is formed on the side of the opening portion 19 of the upper portion of the bag 16. This outlet 25 is connected to one end of the flexible tube 24 through another connecting member 15 in the same way as the blood collecting bag described above. The other end of this tube 24 is connected to the bifurcated end of the bifurcated connector 22. Therefore, the platelet accommodating section 18 of the PC bag 16 communicates with the blood component accommodating section 3 of the blood collecting bag 1 and the plasma accommodating section 12 of the plasma bag 10, respectively, through the tubes 14, 21, 23 and 24 and the bifurcated connectors 20 and 22.

Between the blood collecting bag 1 and the plasma bag 10, there is provided a buffy coat bag 27 which is used to accommodate bully coat temporarily. The buffy coat bag 27 is also formed into a closed bag by laminating flexible sheets of a resin material such as soft polyvinyl chloride and further bonding a peripheral sealing portion 28 thereof in accordance with fusing method (e.g., thermal fusion, high frequency fusion, etc.). In the space defined by the sheets and enclosed by the sealing portion 28, a buffy coat accommodating section 29 is formed to accommodate buffy coat separated from the blood in the blood collecting bag 1.

On the upper portion of the buffy coat bag 27, one end of another flexible tube 26 is connected so as to communicate with the buffy coat accommodating section 29 of the buffy coat bag 27. The other end of this tube 26 is connected to the bifurcated end of the bifurcated connector 20. Therefore, the bully coat accommodating section 29 of the buffy coat bag 27 communicates with the blood component accommodating section 3 of the blood collecting bag 1, the plasma accommodating section 12 of the plasma bag 10, and the platelet accommodating section 18 of the PC bag 16, respectively, through the tubes 14, 21, 23, 24 and 26 and the bifurcated connectors 20 and 22.

In use of the multiple bag system as described above, the blood collecting needle 8 is first inserted into a vein of a donor, and the blood is introduced into the blood component accommodating section 3 of the blood collecting bag 1 through the tube 6 and then stored therein. When the blood within the blood component accommodating section 3 reaches a predetermined quantity, the needle 8 is pulled out from the vein of the donor. Thereafter, the midway portion of the tube 6 is fused for instance to seal it, and the tube 6 on the side of the blood collecting needle 8 is cut off for removal. Under these conditions, the blood is accommodated within the blood collecting bag 1 in airtight condition.

In the above description, explanation is made with reference to the quadruple bag system. However, the multiple bag system to which the present invention is applied is not limited to only the quadruple bag system. That is, this invention can be applied to various bags, such as a single bag only having a blood collecting bag; a double bag system composed of a blood collecting bag and a plasma bag; a triple bag system composed of a blood collecting bag, a PC bag and a plasma bag; and a quadruple bag for use in the different purpose from that of the afore-mentioned quadruple bag. Further, this invention can also be applied to a double bag system, a triple bag system and a quadruple bag system connected to another bag for collecting cryoprecipitate (AHF), for instance.

Furthermore, this invention can also be applied to a multiple bag system having the blood collecting bag 1 in which a first discharge port and a second discharge port which are communicated with the upper portion and the bottom portion of the blood collecting bag, respectively, are formed in such a manner that the plasma in the upper layer is discharged from the first discharge port, the erythrocyte in the lower layer is discharged from the second port, and the bully coat in the middle layer remains in the bag. As one of the examples of such a multiple bag system, one disclosed in U.S. Pat. No. 5,102,407 can be used.

Moreover, a multiple bag system as disclosed In EP-A-484,751 or Japanese Laid-open Patent Publication No. 4-350556 can be used in particular with reference to the embodiment shown in FIGS. 5 and 6 of this application which are described later.

Figure 2:
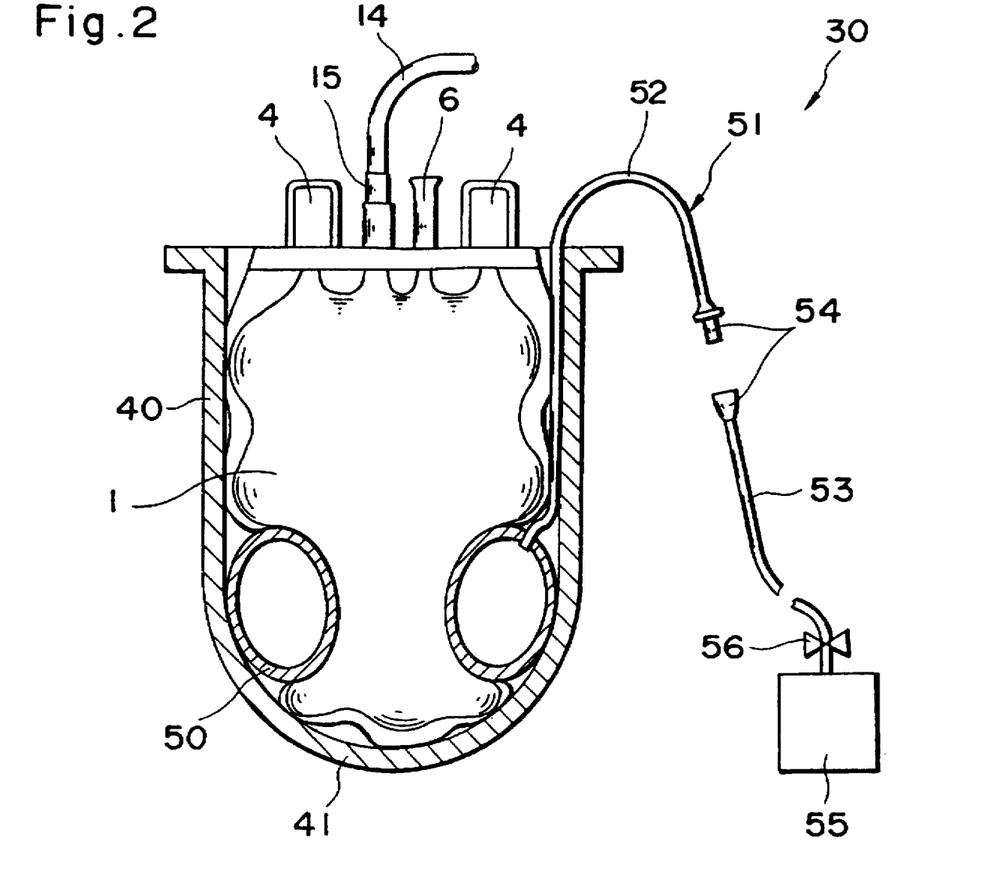
FIG. 2 is a side cross-sectional view showing the first embodiment of the apparatus according to the present invention.

FIG. 2 is a side cross-sectional view showing the first embodiment the separated component transferring apparatus according to the present invention. As shown in the drawing, the apparatus 30 is provided with a centrifugal container (inner cup) 40 in which connected bags of the multiple bag system is to be placed. This centrifugal container 40 is formed into a cylindrical configuration having a bottom and adapted to be removably attached to a centrifugal separator. The bottom 41 of this cup 40 is formed into a semispherical shape.

The centrifugal container 40 is formed of a material having a rigidity of such an extent as not to be deformed easily even when it is certrifuged of even when the blood collecting bag 1 accommodated in the container 40 is pressed during tby the pushing means (described later). Preferably, the material is formed of an acrylic resin such as hard polyvinyl chloride, polyethylene, polypropylene, polycarbonate, polymethylmethacrylate (PMMA), or the like; a metal such as stainless steel or aluminum; various glasses or ceramics; or appropriate combinations of any of these materials.

In the centrifugal container 40 as described above, the connected bags having the blood collecting bag in which blood is stored are placed, and then centrifuged. The connected bags are put into the centrifugal container 40 by stacking the respective bags 1, 10, 16 and 27 and by directing the upper portion of the respective bag, that is the side on which the opening portion is formed toward the upper opening portion side of the centrifugal container 40.

When the connected bags are placed in the centrifugal container 40, it is not necessary to place all the bags in the centrifugal container 40. That is, it is possible to separate the blood collecting bag 1 from the remaining connected bags and then to place only the blood collecting bag 1 in the centrifugal container 40. For this reason, hereinafter, description is made based on a case where only the blood collecting bag 1 is placed in the centrifugal container 40.

Further, the method of removably setting the centrifugal container 40 to the centrifugal separator is not particularly limited. For example, the centrifugal container 40 may be constructed such that the container 40 is supported at opposite two portions of the upper annular edge thereof (not shown) so as to be rotatable with respect to the axis extending through the two supported portions.

The separated component transferring apparatus 30 according to the present invention is provided with a pressing means for pressing the blood collecting bag 1 in which blood is contained. In the first embodiment shown in FIG. 2, the pressing means is composed of an expansible and contractible cuff 50 to be interposed between the inner surface of the centrifugal container 40 and the outer surface of the blood collecting bag 1, and a fluid supplying means 51 for supplying a fluid such as air into the cuff 50 for expansion thereof.

Figure 3:
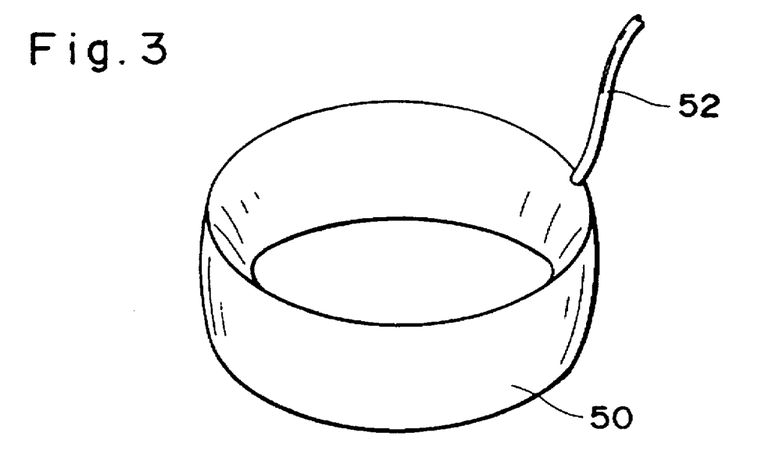
FIG. 3 is a perspective view showing a cuff as pressing means of the first embodiment.

The cuff 50 Is formed into an annular tubular shape so as to be able to push or press the outer circumferential surface of the blood collecting bag 1 roughly uniformly. As shown in FIG. 3, the cuff 50 is constituted so as to provide a central space under the contracted condition thereof into which the blood collecting bag 1 containing the blood can be passed therethrough.

The cuff 50 is formed of a sheet material made of various rubbers (e.g., silicone rubber, etc.), various resins (e.g., soft polyvinyl chloride, polyethylene, polypropylene, etc.), cloth, and any appropriate combinations of these materials.

The dimensions of the cuff 50 are not limited to specific values. However, it is preferable to determine the width W of the cuff 50 within a range between 50 mm and 100 mm, in particular between 70 mm and 90 mm.

Further, the cuff 50 may be fixed to either the inner surface of the centrifugal container 40 or the outer surface of the blood collecting bag 1. Alternatively, the cuff 50 is simply interposed between the centrifugal container 40 and the blood collecting bag 1. Further, the shape of the cuff 50 is not limited only to the annular shape as shown. For instance, it Is possible to arrange a pair of flat bags on the front and rear sides of the blood collecting bag 1, respectively.

The fluid supplying means 51 is composed of an air feeding tube 52 communicating with the inner side of the cuff 50; an air supply source 55 such as air cylinder, air compressor, compressed gas cylinder, etc.; another air feeding tube 53 connected to the air supply source 55; a pair of male and female connectors 54 connected between the two air feeding tubes 52 and 53; and open and close valve 56 disposed midway of the air feeding tube 53 to control the air supplied into the cuff 50. In this case, the open and close valve 56 may be constructed into the type in which the air pressure supplied to the cuff 50 can be adjusted by adjusting the opening rate thereof.

Further, the fluid for expanding the cuff 50 is not limited to only air, and other gas or water can be used.

The operation of the separated component transferring apparatus as described above will be described hereinbelow.

In order to place the blood collecting bag 1 in the bag accommodating container 40 or centrifuge the blood collecting bag 1, first, the connector 54 is removed from the cuff 50 to contract the cuff 50.

Next, The blood collecting bag 1 in which blood is contained is placed in the centrifugal container 40, and the centrifugal container 40 accommodating the blood collecting bag 1 is then set to the centrifugal separator (not shown) for centrifugal separation. Therefore, the blood in the blood collecting bag 1 is separated into three layers of a plasma layer, a buffy coat layer, and an erythrocyte layer in this order from the above.

After the centrifugal separation, under the condition that the blood collecting bag 1 is kept placed in the centrifugal container 40, the centrifugal container 40 is removed from the centrifugal separator, and further fixed to a fixing means (not shown) such as a stand or a mounting base. In this state, since the blood collecting bag 1 is not removed from the centrifugal container 40, the interfaces between two of the respective separated components are not disturbed. In this case, it should be noted that in the case where all the connected bags in the double, triple, or quadruple bag system are placed in the centrifugal container 40 for centrifugal separation, the bag or bags other than the blood collecting bag 1 are removed from the centrifugal container 40.

Successively, the plasma in the upper layer is collected from the separated components. In this case, the connecting member 15 of the upper portion of the blood collecting bag 1 is broken to allow the fluid communication and further the tube 26 is closed by a clamp or an electrically actuated solenoid pinch valve or the like. On the other hand, the connector 54 is connected. The air supply source 55 is actuated and the open and close valve 56 is opened, to feed air into the cuff 50 through the feeding tubes 52 and 53, so that the cuff 50 is expanded. In accordance with the expansion of the cuff 50, the blood collecting bag 1 is pressed and thereby the inner pressure thereof increases. With this result, the upper plasma layer is discharged through the outlet 5, and further fed into the plasma bag 10 through the tubes 14, 21 and 23, respectively. When the plasma is being discharged, the blood collection bag 1 is kept under the expanded condition, as already explained. Therefore, the lower components will not mixed with the plasma now being discharged and fed, thus improving the yield for the collection of the plasma.

In this case, the discharging speed of the plasma from the blood collecting bag 1 is preferably set in the rate under which no eddy that is likely to disturb the interface between the respective separated components is caused in the blood collecting bag 1 and the time required for the collection of the plasma can be shortened as much as possible. The control of the discharging speed of the plasma can be conducted, for example, by controlling the pressure of the actuating fluid to be supplied to the cuff 50.

In the separated component transferring apparatus 30 shown in FIG. 2, there are advantages such as follows. Namely, in this apparatus, the conventionally used centrifugal cup (inner cup) can be used as it is as the centrifugal container 40 by inserting the cuff 50 therein, in which the actuating fluid is supplied into the cuff 50 through the fluid supply means 51. Therefore, it becomes possible to make the whole structure thereof simple. In addition, since there is no mechanically operated structure required for reciprocal or rotational motion of the pressing means as performed in the pressing means of the embodiments shown in FIGS. 4, 5, 6 and 7, there is less possibility that any trouble would be happened. Further, since the pressing rate to the blood collecting bag 1 can be adjusted appropriately by controlling the pressure of the actuating fluid to be supplied to the cuff 50, the adjustment of the discharging speed of the separated component can be made with high accuracy. Furthermore, if a long tube is used as the respective air feeding tube 52, 53, it becomes possible to remote control the pressing motion against the blood collecting bag 1.

In this embodiment, it is possible to use a sucking means (not shown) together with the pressing means for pressing the blood collecting bag 1. In this case, since the quantity of plasma discharged per unit time can be increased while keeping the high yield, it is possible to shorten the time required to collect the separated components.

Figure 11:
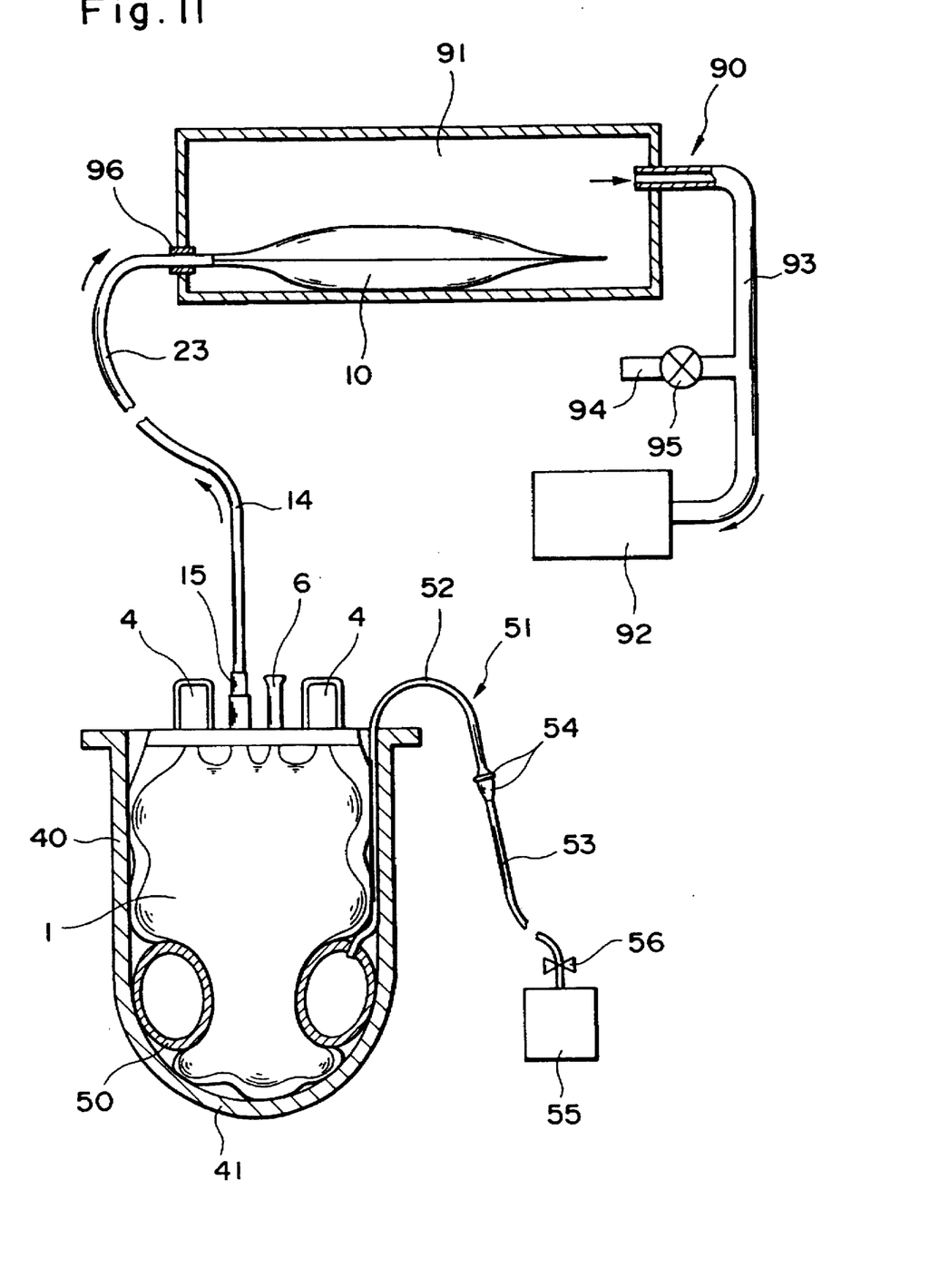
FIG. 11 is a side cross-sectional view showing the example in which the sucking means is additionally provided to the first embodiment.

FIG. 11 is a cross-sectional view showing one example of the sucking means. The sucking means 90 shown in the drawing comprises a vacuum chamber 91, a vacuum pump 92, a pipe 93 connected between the vacuum chamber 91 and the vacuum pump 92. On the middle portion of the pipe 93, there is formed a branch pipe 94, on which a valve 95 is provided.

In the vacuum chamber 91, the plasma bag 10 which is a container for collecting the separated plasma is adapted to be placed. The tube 23 connected to the plasma bag 10 passes through a wall portion of the vacuum chamber 91 through a seal member. For this structure, the vacuum chamber 91 can be kept air-tight.

When the vacuum pump 92 is actuated under the condition that the valve 95 is closed, the air in the vacuum chamber 91 is discharged through the pipe 93, and therefore the inner pressure of the vacuum chamber 91, that is, the atmosphere around the plasma bag 10 is reduced to be a negative pressure. Due to this reduced pressure, the plasma is sucked into the plasma bag 10. In this case, it is preferable to maintain the inner pressure of the vacuum chamber 91 to a constant value or within a predetermined value during the sucking operation. The adjustment of the inner pressure of the vacuum chamber 91 is made for example by on-off operation of the vacuum pump 92, open-close operation of the valve 95, or adjustment for the opening rate of the valve 95. The reduced inner pressure of the vacuum chamber 91 during the sucking operation is for example set to the rate between −100 mmHg and −300 mmHg (here, 0 mmHg is equal to the atmospheric pressure).

As an alternative to the sucking means, it is possible to provide a roller pump provided on the midway of the tube 14 connected to the blood collecting bag 1. The roller pump is adapted to squeeze the tube 14 so as to transfer the liquid within the tube to the side of the plasma bag 10.

In these cases, it is preferable that the quantity of air to be sucked is set to such an extent that a rising in the inner pressure of the blood collecting bag 1 by the pressing means is not reduced markedly.

Further, after almost all the quantity of the plasma is discharged from the blood collecting bag 1, the tube 21 is closed by a clamp or a solenoid pinch valve, while the tube 26 is opened. When the blood collecting bag 1 is further pressed under this condition in the same way as above, the intermediate buffy coat layer can be discharged. The buffy coat layer is fed into the bully coat bag 27 through the tubes 14 and 26, respectively.

Upon discharging the bully coat layer from the blood collecting bag 1, it is also possible to additionally provide such a sucking means as described above. In this case, the bully coat bag 27 which is a container for collecting the bully coat layer is placed inside the vacuum chamber 91 of the sucking means 90.

In this embodiment, it is possible to provide an optical sensor 80 at the midway of the tube 14 to detect the fact that almost all the quantity of the plasma in the blood collecting bag 1 has been discharged. This optical sensor 80 is constituted from light emitting element and light receiving element which are disposed on the opposite sides of the tube 14. When almost all the quantity of the plasma has been discharged from the blood collecting bag 1 and therefore the liquid flowing within the tube 14 is changed from the plasma to the bully coat, the permeability of the light emitted from the light emitting element is reduced and therefore the amount of the light received by the light receiving element is also reduced. At this point of time, the fact that almost all the quantity of the plasma in the blood collecting bag 1 has been discharged is detected.

When the fact that almost all the quantity of the plasma is discharged from the blood collecting bag 1 is detected by the way described above, the transfer of the plasma to the plasma bag 10 is stopped by closing the tube 21 by clamping the midway of the tube 21 by a clamp or by actuating the solenoid pinch valve through the control performed by a micro computer (not shown). Thereafter, by opening the fluid path to the bully coat bag 27, fluid communication is changed so as to allow the bully coat is fed or transferred into the bully coat bag 27. In this state, the actuating fluid from the fluid supply means 51 to the cuff 50 is supplied continuously, so that the bully coat is being discharged from the blood collecting bag 1.

The weight of the bully coat bag 27 is kept monitored by a weight sensor such as a load cell (not shown). When the weight sensor detects the fact that the weight of the buffy coat stored in the buffy coat bag 27 reaches at a predetermined value, the transfer of the buffy coat from the blood collecting bag 1 to the buffy coat bag 27 is stopped.

The discharge of the buffy coat from the blood collecting bag 1 is stopped by stopping the supply of the actuating fluid from the fluid supply means 51 to the cuff 50 or closing the tube 14 or 26 with a clamp or the like. The supply of the actuating fluid is stopped by closing the valve 56 or stopping the operation of the air supply source 55.

As stated in the foregoings, if the apparatus is constituted such that the discharge of the blood component from the blood collecting bag 1 can be stopped or changed so as to direct toward a different bag in good timing based on the detected information by the optical sensor 80 or the weight sensor, the yield for the component is further improved.

Figure 4:
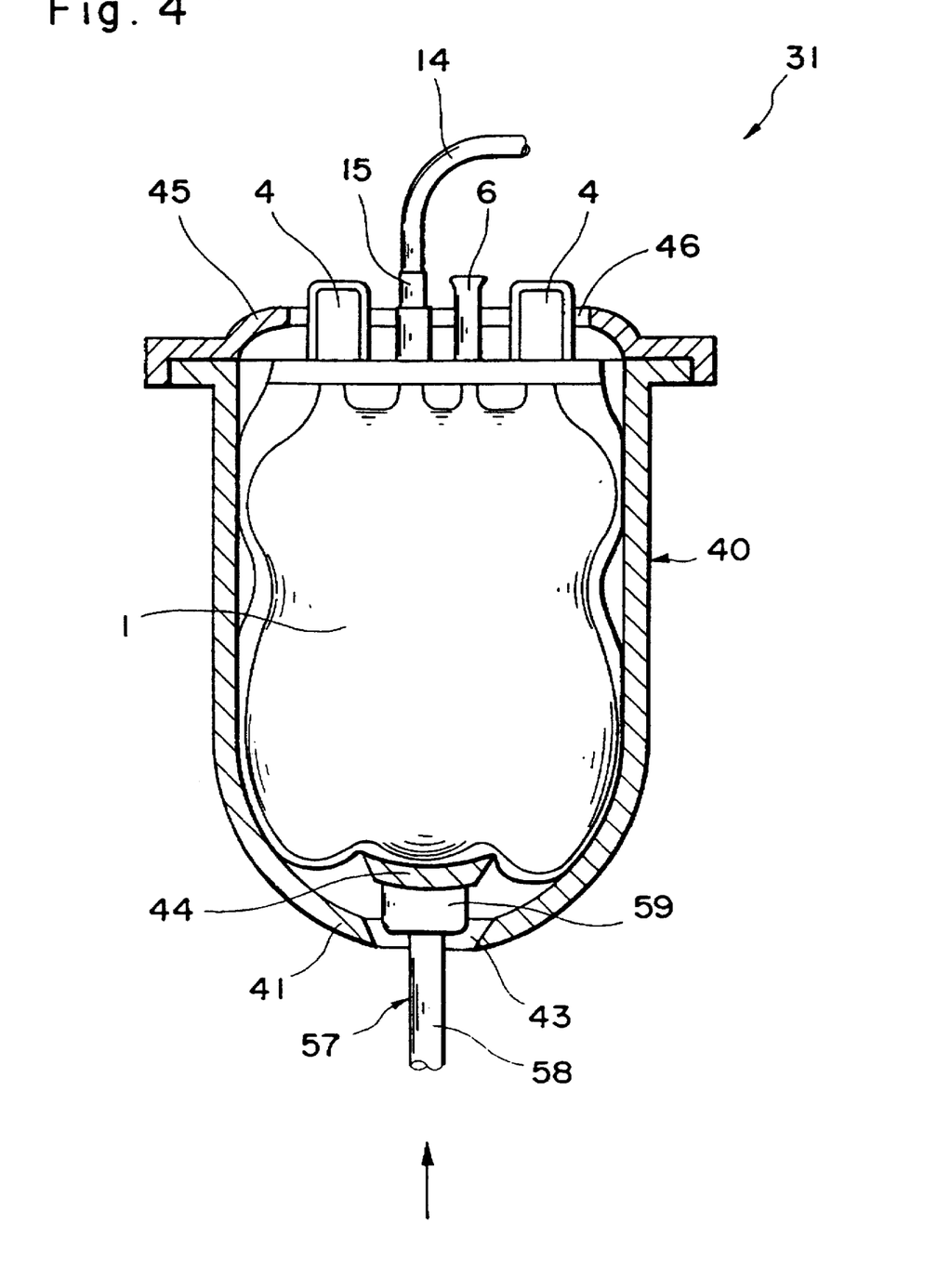
FIG. 4 is a side cross-sectional view showing the second embodiment of the apparatus according to the present invention.

FIG. 4 is a side cross-sectional view showing the second embodiment of the separated component transferring apparatus according to the present invention. In the separated component transferring apparatus 31 shown in FIG. 4, the centrifugal container 40 is formed with an opening 43 at a bottom portion 41 thereof, and a closure member 44 for shielding the opening 43 is disposed so as to be able to close the opening 43.

The edge portions of the opening 43 and the closure member 44 are both formed into a tapered shape, respectively so as to be fitted to each other. Further, the closure member 44 is so formed as to be removable from the opening 43 only in the inner direction of the centrifugal container 40. For this structure, the closure member 44 can securely cover the opening 43 during the centrifugal separation, thereby preventing the lower portion of the blood collecting bag 1 from being projected through the opening 43.

On the other hand, a lid 45 is removably attached to the upper portion of the centrifugal container 40. This lid 45 serves to prevent the blood collecting bag 1 from being moved upwardly away from the centrifugal container 40, when the blood collecting bag 1 is pressed by a push member 57 (described later) in the arrow direction. The lid 45 is formed with a slit-like opening 46 so that the tubes 6 and 14 and the opening portions 4 of the blood collecting bag 1 can project therethrough.

The lid 45 can be attached to the centrifugal container 40 after or before the centrifugal separation. In the separated component transferring apparatus 31 of this embodiment, the pressing means is composed of a push member 57 for pushing the blood collecting bag 1, and a driving means (not shown) for driving the push member 57.

The push member 57 is composed of a piston 58 movable in the up and down directions in FIG. 4, and a head 59 fixed to the end of the piston 58. In accordance with the pressing means as constructed above, when the piston 58 is moved upwardly by the driving means as shown in FIG. 4, the upper surface of the head 59 raises the closure member 44 and then the head 59 is inserted into the opening 43 together with the closure member 44. With this result, the blood collecting bag 1 is pressed from the lower side thereof to discharge the plasma in the upper layer in accordance with the processes as described already.

As the driving means, a mechanism for moving the piston 58 up and down may be used. For example, an air cylinder; a hydraulic cylinder; a step motor; a motor provided with a crank mechanism, a cam mechanism, or a mechanism composed of rack and pinion gear; or a mechanism driven reciprocatingly by manual operation can be used.

In accordance with the embodiment shown in FIG. 4, the following advantages are realized. Namely, according to this embodiment, it is possible to use a centrifugal container made of a ridged material. Further, except for the operation required for mounting the lid 45 to the upper portion of the centrifugal container 40, no other operation is required upon the centrifugal separation. Furthermore, as described in the above, since the driving means is formed from a mechanism which can effect only the reciprocal motion, it can be formed into a relatively simple structure. Moreover, the driving means is constructed so as to press or push the blood collecting bag 1 from the lower side thereof, the space extending in the horizontal direction is not necessary.

Figure 5:
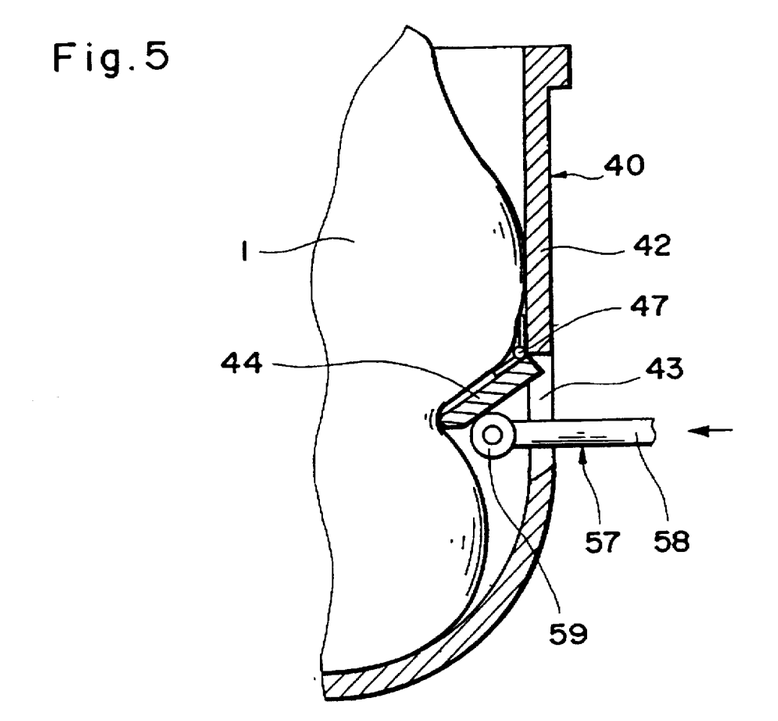
FIG. 5 is a partial side cross-sectional view showing a modification of the second embodiment.

Further, without being limited to the bottom portion 41 of the centrifugal container 40, the opening 43 can be formed in a side portion 42 of the centrifugal container 40 as the modification of the second embodiment shown in FIG. 5. In this case, a closure member 44 for covering the opening 43 is attached to the wall of the centrifugal container 40 through a hinge 47 so as to be opened only in the inward direction of the centrifugal container 40. In accordance with this modification, it is possible to prevent the side portion of the blood collecting bag 1 from being projected from the opening 43 during the centrifugal separation in the same way as the second embodiment as described above.

In the separated component transferring apparatus according to this modification, the pressing means is composed of a push member 57 for pushing the blood collecting bag 1, and the driving means (not shown) for driving the push member 57 in the same way as already explained. In this case, the push member 57 is moved in the right and left direction in FIG. 5. When the piston 58 is moved in the leftward direction by the driving means, the head 59 pushes the closure member 44 to open it. When the head 59 is further inserted into the opening 43 to press the blood collecting bag 1 from the lateral side thereof, the plasma in the upper layer can be discharged in the same way as described already.

In accordance with the modification described in FIG. 5, the following advantages are realized. Namely, according to this modification, it is possible to use a centrifugal container 40 formed of a ridged material in the same way as the embodiment shown in FIG. 4. Further, since the opening 43 is formed on the side wall of the centrifugal container 40, durability of the container 40 is improved in view of the fact that a relatively less centrifugal force is exerted on the closure member 44 during the centrifugal separation. Furthermore, it is not necessary to provide with a lid on the upper portion of the centrifugal container 40 like the lid 45 of the embodiment shown In FIG. 4.

Figure 6:
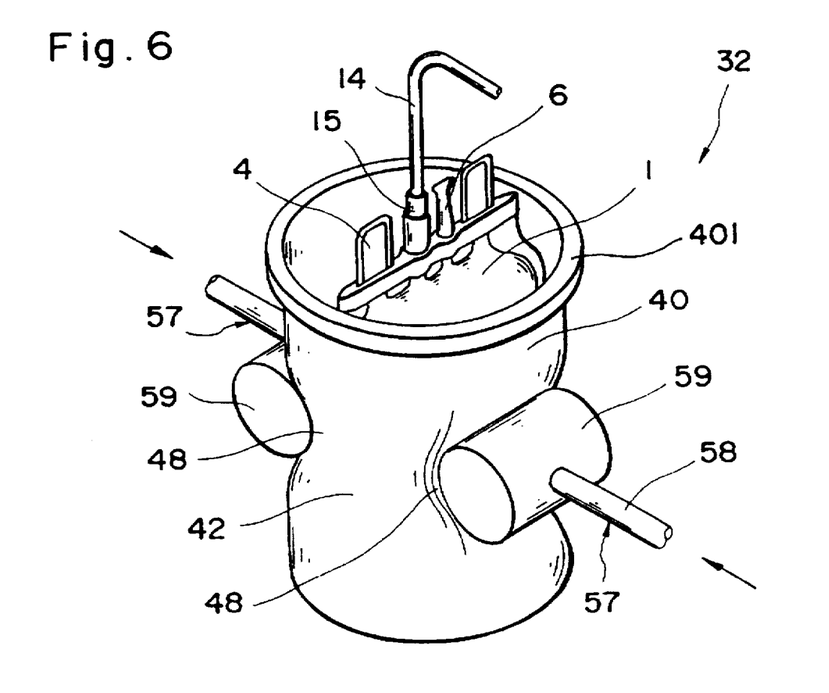
FIG. 6 is a perspective view showing the third embodiment of the apparatus according to the present invention.

FIG. 6 is a perspective view showing the third embodiment of the separated component transferring apparatus according to the present invention. In the apparatus 32 shown in FIG. 6, at least one part of the centrifugal container 40, that is, the side portion 42 thereof is formed of a soft material to provide a soft material part 48. When this soft material part 48 is pressed by the push member 57 as described above, the soft material part 48 is deformed so as to project in the inner direction of the centrifugal container 40.

The pressing means of this embodiment is composed of a pair of push members 57 and the driving means (not shown) for driving the push members 57 both roughly in the horizontal direction. When two opposing pistons 58 are moved in the direction that both the heads 59 approach each other, the soft material part 48 of the centrifugal container 40 is pressed by the two heads 59 and then deformed in the inner direction of the centrifugal container 40. As a result, the blood collecting bag 1 placed in the centrifugal container 40 is also compressed, so that the plasma in the upper layer is discharged from the blood collecting bag 1.

In this embodiment, it should be noted that the pressing means is constructed such that one of the push members 57 is not movable and only the other push member 57 is movable so as to press the soft material part 48 of the centrifugal container 40.

The soft material part 48 of the centrifugal container 40 is formed of a soft synthetic resin like a polyester such as soft polyvinyl chloride, polyethylene, polypropylene, polyethyleneterephtalate, or a combination of these materials. Further, the soft material part 48 can be formed at a bottom portion 41 of the centrifugal container 40, without being limited to only the side portion 42 thereof as described in the drawing.

As one of the example of the centrifugal container 40 used in the apparatus 32 of this embodiment, a portion excepting a frame portion 401, that is, a cylindrical portion thereof can be formed of the soft material as described above.

Further, any types of the pressing means such as rollers, fastening members, etc. can be used instead of the pair of the heads 59 as described above, as far as the soft material part 48 of the centrifugal container 40 can be deformed inwardly. Further, it is also possible to construct the pressing means from the above described cuff to be disposed around the soft material part 48 and the fluid supply means 51 for supplying the fluid to the cuff to expand it.

In accordance with the separated component transferring apparatus 32 of this embodiment as shown in FIG. 6, there are advantages such as follows. Namely, according to this embodiment, the blood collecting bag 1 can be pressed from the front and rear side thereof, the interfaces between the respective component layers is kept more stationary when the separated component is being discharged, thus leading to improvement of the yield for the blood component. Further, since the driving means of this embodiment is formed from the mechanism which merely perform reciprocal motion, the mechanism can be constructed with simple structure.

Figure 7:
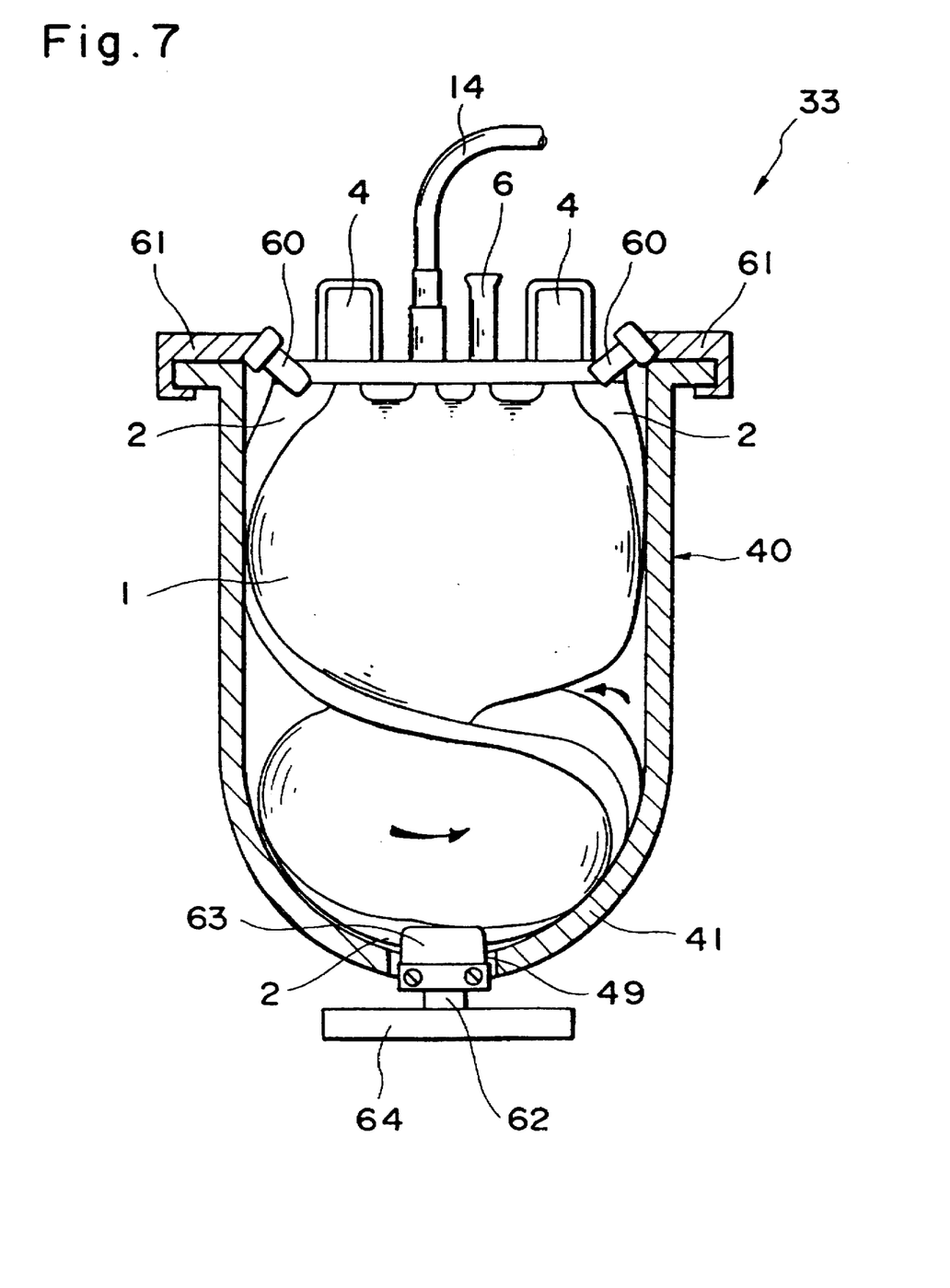
FIG. 7 is a side cross-sectional view showing the fourth embodiment of the apparatus according to the present invention.

FIG. 7 is a perspective view showing the fourth embodiment of the separated component transferring apparatus according to the present invention. In the separated component transferring apparatus shown in FIG. 7, the pressing means is composed of a member for fixing the upper end portion of the blood collecting bag 1 to the centrifugal container 40, and a rotating means for twisting the blood collecting bag 1 by rotating the lower portion of the blood collecting bag 1.

In more detail, on the upper portion of the centrifugal container 40, there are disposed two clips 60 which are fixed to the opposite end portions of the centrifugal container 40 with an appropriate fixing member 61, respectively. The seal portions 2 of the opposite upper sides of the blood collecting bag 1 are fixedly supported by the clips 60, respectively.

In this case, in a case where the fixing member 61 is constructed so as to be removable from the centrifugal container 40, the fixing member 61 can be attached to the centrifugal container before or after the centrifugal separation. Further, the blood collecting bag 1 can also be attached to the clips 60 before or after the centrifugal separation.

On the other hand, the centrifugal container 40 is formed with an opening 49 at the bottom portion 41 thereof, into which another clip 63 fixed to an end of an axis 62 is inserted. A lower seal portion 2 of the blood collecting bag 1 is held by the clip 63. Further, a handle 64 is fixed to the base end of the axis 62.

As shown in FIG. 7, when the handle 64 is rotated in a predetermined direction, the lower end of the blood collecting bag 1 is also rotated. In accordance with the rotation of the lower end of the blood collecting bag 1, the bag 1 is twisted, so that the blood collecting bag 1 is compressed to discharge the plasma in the upper layer.

In this embodiment, the handle 64 can be rotated by use of various motors or rotating device having a variable speed mechanism, or by manual operation.

Further, in order to avoid that the handle 64 which has been rotated is reversed due to the restoring force generated to the blood collecting bag 1, an one-way clutch mechanism composed of a ratchet mechanism or the like (not shown) can be additionally provided.

In accordance with the separated component transferring apparatus 33, there is an advantage that the pressing means can be formed from a simple structure even when the handle 64 is rotated by the rotating device. Further, since the rotating device is different from the mechanisms shown in FIGS. 4, 5 and 6 which perform the reciprocal motion, space for allowing the reciprocal motion is not necessary, so that miniaturization of the apparatus can be achieved due to no laterally expanding space being required.

Figure 8:
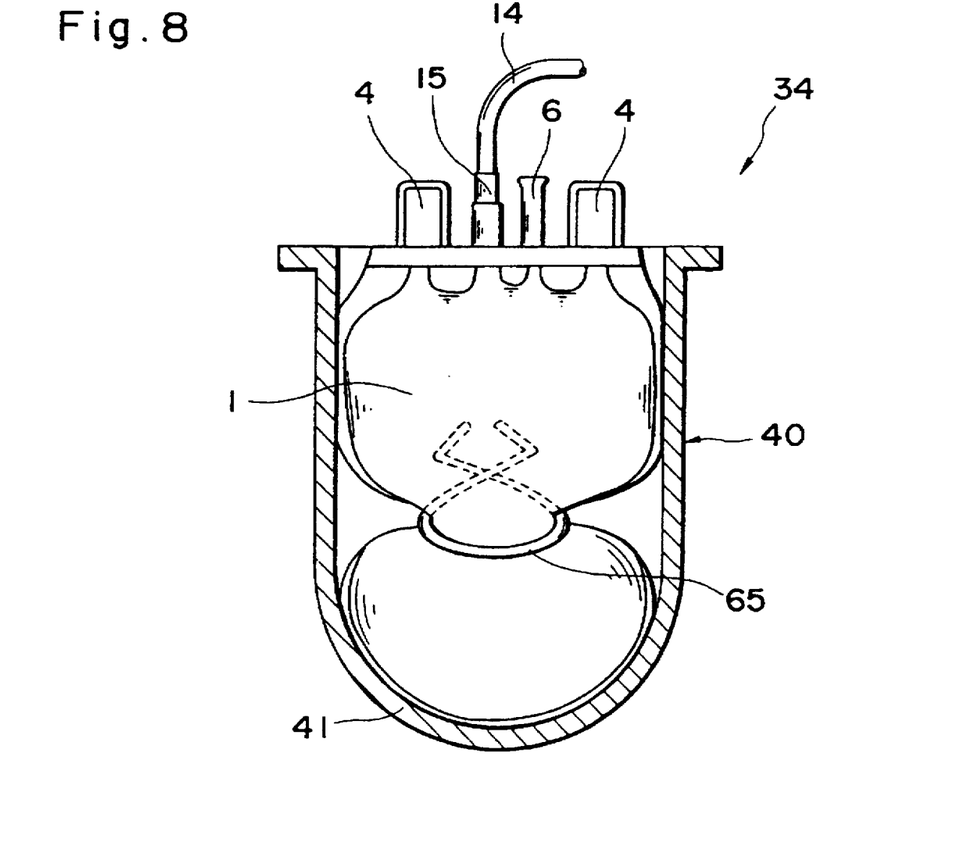
FIG. 8 is a side cross-sectional view showing the fifth embodiment of the apparatus according to the present invention.
Figure 9:
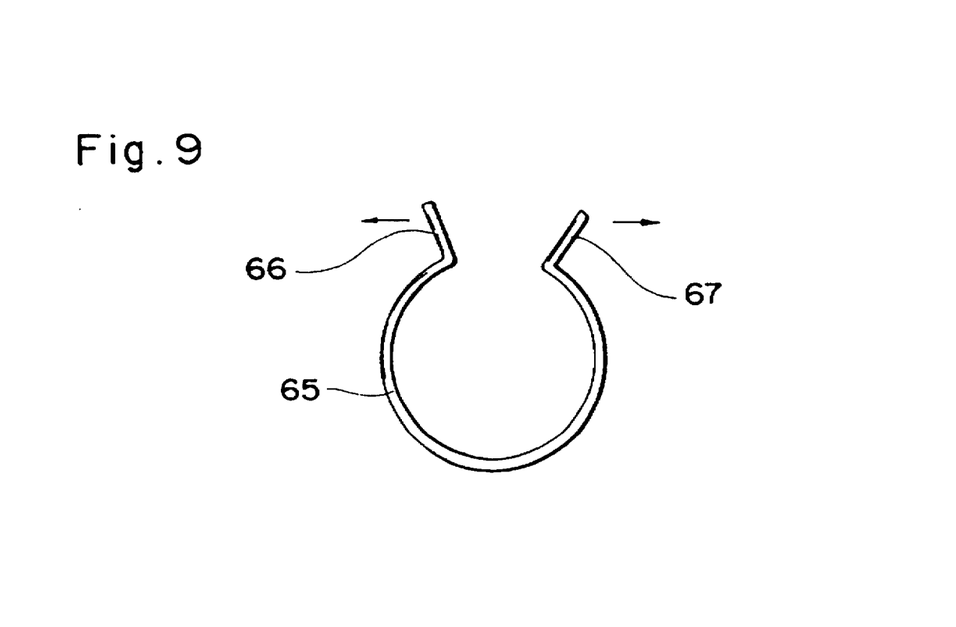
FIG. 9 is a plan view showing the pushing means of the fifth embodiment.

FIG. 8 is a perspective view showing the fifth embodiment of the separated component transferring apparatus according to the present invention. In the separated component transferring apparatus 34 shown in FIG. 8, the pressing means is composed from a fastening member 65 for pressing the outer circumferential surface of the blood collecting bag 1. As shown in FIG. 9, this fastening member 65 is formed by bending a resilient material such as a metallic wire into a substantially annular ring shape. The fastening member is adapted to be able to keep such a configuration as shown In FIG. 8 under the natural condition (no external force is applied thereto).

The fastening member 65 functions as follows. Namely, the fastening member 65 is first expanded as shown in FIG. 9, and then set to the outer circumferential surface of the blood collecting bag 1 before the centrifugal separation. The blood collecting bag 1 is placed in the centrifugal container 40 under that condition, and then centrifugal separation is taken place. Since the blood collecting bag 1 is fastened tightly by the fastening member 65 in such a way that the trunk portion thereof is compressed, so that the blood collecting bag 1 is pressed. Accordingly, when the connecting member 15 is broken to effect the fluid communication therethrough, the separated plasma in the upper layer can be discharged and transferred automatically toward the plasma bag collection due to the increased inner pressure of the blood collecting bag 1.

In this embodiment, it is also possible to keep the fastening member 65 to the expanded condition shown in FIG. 9 with a fixing member (not shown) during the centrifugal separation. The expanded condition of the fastening member 65 by the fixing member is released when the plasma is to be discharged, so that the trunk portion of the blood bag 1 is then fastened by the fastening member to compress it.

Further, the fastening member 65 may be constructed such that the inner diameter is reduced by applying an external force by which one end 66 and the other end 67 of the fastening member 65 approach to each other, without using the structure that compresses the blood collecting bag 1 by use of the resilient force of the fastening member 65 in itself as described in the above. In this case, as the means for applying the external force, a mechanism having a drive means which moves one end 66 and/or the other end 67 of the fastening member 65 can be used. The driving means is preferably formed from a motor, an air cylinder, or a hydraulic cylinder or the like. Alternatively, a mechanism which attracts one end 66 and/or the other end by use of an electric magnet when it is energized can also be used.

In this embodiment, a single or plural fastening members 65 having the structure as described above can be used for a single blood collecting bag 1.

Further, it is also possible to wind a string around the outer circumferential surface of the blood collecting bag 1 and to apply a tension thereto for fastening the bag 1, instead of the fastening member 65 of the metallic wire as described above.

Furthermore, it is also possible to adopt such pressing means that sandwiches the blood collecting bag 1 by a pair of plate-shaped sandwiching members in which the distance between the two sandwiching members can be reduced with an adjusting screw, for instance.

In accordance with the separated component transferring apparatus of the embodiment shown in FIG. 8, there are advantages such as follows. Namely, according to the embodiment, a conventionally used centrifugal cup can be used as the centrifugal container 40. Further, in order to press the blood collecting bag 1, it is not necessary to provide another device outside the centrifugal container 40 like the fluid supply means 51 of the first embodiment. As a result, the structure of the pressing means can be made simply, thus enabling to make the size of the apparatus small.

Figure 10:
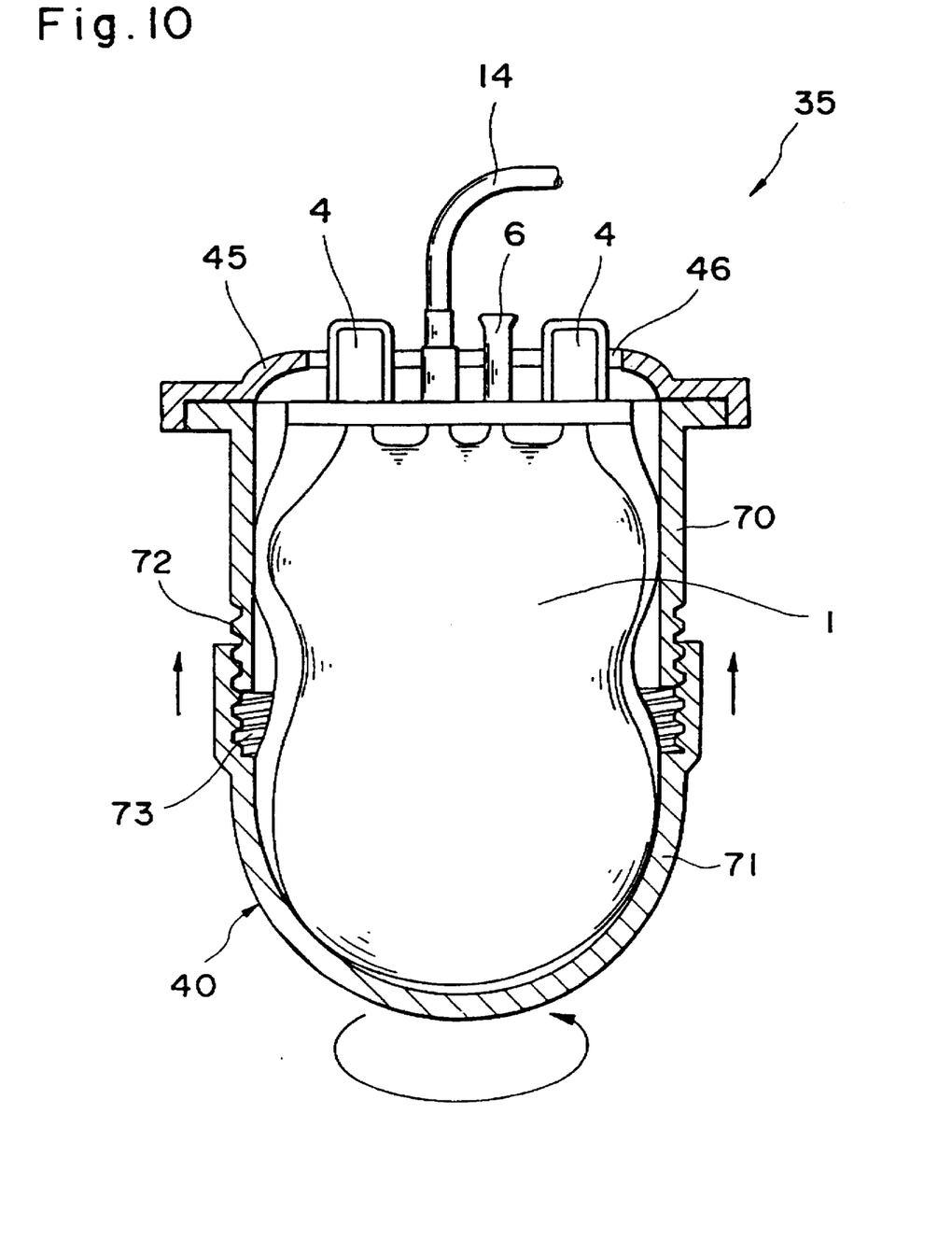
FIG. 10 is a side cross-sectional view showing the sixth embodiment of the apparatus according to the present invention.

FIG. 10 is a perspective view showing the sixth embodiment of the separated component transferring apparatus according to the present invention. In the separated component transferring apparatus 35 shown in FIG. 10, the centrifugal container 40 is composed of two members of upper half cup body 70 and lower half cup member 71. The cup bodies 70 and 71 are adapted to be assembled integrally with each other with the use of male and female threads 72 and 73, respectively. Further, a lid 45 which is removable from the centrifugal container 40 is attached to the upper portion of the centrifugal container 40.

The lid 45 can be attached to the centrifugal container before or after the centrifugal separation.

In the separated component transferring apparatus 35 as described above, when one of the upper and lower half cup bodies 70 and 71 is rotated relative to the other, the centrifugal container 40 can be extended or retracted relative to each other by the threading motion, so that the depth of the centrifugal auxiliary cup 40 changes. For example, when the upper half cup body 70 is fixed and the lower half cup body 71 is rotated in the direction that the centrifugal container 40 is retracted, the lower half cup body 71 raises relative to the upper half cup body 70. In accordance with the raise of the lower half cup body 71, the blood collecting bag 1 placed in the centrifugal container 40 is compressed since it is sandwiched between the inner surface of the lid 45 and the bottom portion 41 of the centrifugal container 40, so that the plasma in the upper layer is discharged as described already.

In this embodiment, the lower half cup body 71 can be rotated by e.g. various motors, rotating device having rotational speed change mechanism or manual operation.

Further, it is also possible to form the centrifugal container 40 in such a way that a bellows or an appropriate slide mechanism, which function as the pressing means, is disposed at the middle portion thereof so as to be extendable and retractable. In this case, it is preferable to provide a stopper for stopping the extendable and contractible motion of the centrifugal container 40 during the centrifugal separation.

In accordance with the embodiment as described above, there are advantages such as follows. Namely, the apparatus of this embodiment can be constructed from a simple structure even when the lower half cup body 71 is rotated by the driving device. Of course, when the lower cup body 71 is rotated by manual operation, other device is not necessary. Further, the pressing means of this embodiment is different from the mechanism which performs reciprocal motion as is done in the embodiments shown in FIGS. 4, 5 and 6. Therefore, this embodiment does not need a space for the reciprocal motion, thus enabling to miniaturize the size of the apparatus. Furthermore, according to this embodiment, it is possible to press or push the bottom portion of the blood collecting bag 1 wholly and uniformly. With this result, the interfaces between the respective blood components are kept more stationary when the separated component is discharged, thereby enabling to improve the yield of the collected blood component. Moreover, it is also possible to adjust the depth of the centrifugal container 40 to the most appropriate length in accordance with the various conditions such as the size of the blood collecting bag 1 or the quantity of the fluid in the bag, before the centrifugal separation or before pressing the blood collecting bag 1 after the centrifugal separation.

The separated component transferring apparatus according to the present invention has been described with reference to the embodiments as shown in the attached drawings. However, the present invention is not limited only to these embodiments. In particular, any types of the pressing means can be adopted by combining the aforementioned examples or other means, as far as the flexible bag placed in the centrifugal container can be pressed.

Further, it should be noted that the sucking means described with reference to FIG. 11 can also be applied to the embodiments other than the first embodiment.

Furthermore, it should be also noted that this invention can be applied to the case other than the transfer of the centrifugally separated blood component. For example, this invention can be used for collecting or taking out a layer including the effective component of eupyrene cells from a bone marrow fluid, for instance.

Hereinafter, practical experiments of the present invention will be described hereinbelow. [Experiment 1]

A quadruple bag system (four-connected bags) as shown in FIG. 1 was manufactured as follows: a blood collecting bag (400 ml in volume), a PC bag (60 ml in volume), a plasma bag (300 ml in volume) and a bully coat bag (60 ml in volume) are all manufactured by use of a soft polyvinyl chloride sheet with a thickness of 0.39 mm. Further, these bags are connected through soft polyvinyl chloride tubes as shown in FIG. 1.

On the other hand, a centrifugal container 40 as shown in FIG. 2 was manufactured by use of polypropylene. The wall thickness of the container 40 was 2.5 mm, the inner diameter thereof was 95 mm, and the maximum depth thereof was 130 mm.

As the pressing means for pressing the blood collecting bag, an annular cuff (width (W)=80 mm) was formed of soft polyvinyl chloride so as to be expandable and contractible. The annular cuff was placed on an inner surface of the centrifugal container 40 at a position 30 mm away from the bottom of the container 40, and further connected to an air supplying source (i.e. air compressor) through an air feeding tube.

A whole blood was collected in the blood collecting bag of the above-mentioned connected bags, and the blood collecting bag was placed in the centrifugal container under the condition that the annular cuff was contracted together with other bags. Then, the centrifugal container was set to a centrifugal separator (MODEL: DPR-6000 MODEL made by IEC Corp.), and centrifuged under 420 rpm for 5 minutes.

Thereafter, the centrifugal container 40 was removed from the centrifugal separator, and further the bags other than the blood collecting bag were also removed from the centrifugal container 40. The connecting member 15 was then broken to effect the fluid communication therethrough, and further the tube 26 is closed by a clamp. Successively, the compressor was actuated, and compressed air of 0.6 Kg/cm2 is fed into the annular cuff to expand the annular cuff gradually, so that the blood collecting bag in the centrifugal container was pressed to discharge the plasma in the upper layer through the tube 14. The discharged plasma was then transferred and collected into the plasma bag 10.

[Experiment 2]

In this experiment, the connected bags, the centrifugal container and the pressing means which are all the same as with those of the Experiment 1 were used, by which the whole blood was centrifuged under the same conditions as those in Experiment 1.

After the centrifugal separation, the blood collecting bag accommodated in the centrifugal container was pressed in the same way as in Experiment 1, while the plasma bag 10 was placed in a pressure reducing chamber kept at a vacuum of −180 mmHg, to suck the plasma in the upper layer in the blood collecting bag in order to transfer and collect it into the plasma bag 10 through the tube 14.

[Comparative Experiment]

The connected bags and the centrifugal container which are the same as those used in the Experiment 1 were used, but any pushing means was not used. Further, the whole blood was centrifuged under the same conditions as those in Embodiment 1.

Thereafter, the connected bags were removed from the centrifugal container 40, and only the blood collecting bag was set between a pair of plates of a separator stand by hanging a small hole formed in the blood collecting bag on a hook of the separator stand. Then, the blood collecting bag was sandwiched between the two plates of the separator stand for pressurization, to discharge the plasma in the upper layer and transfer and collect it to the plasma bag 10.

The quantities of the blood and the collected plasma, and the time required to collect the plasma were measured. Table 1 below lists these measured results.

TABLE 1

|  | QUANTITY OF BLOOD [g] | QUANTITY OF PLASMA [g] | TIME REQUIRED TO COLLECT PLASMA [sec] |
| --- | --- | --- | --- |
| EXPRMT 1 | 426.2 | 318.4 | 36.0 |
| EXPRMT 2 | 428.3 | 320.2 | 27.5 |
| COMPAR | 424.2 | 314.0 | 97.4 |

As indicated in Table 1, the yield for plasma collection (purity) is high in Experiments 1 and 2, as compared with Comparative Experiment. In particular, in the case of Experiment 2 in which the plasma is collected under the condition that the suction is performed in addition to the pressing motion, the time required to collect plasma can be shortened.

In addition, in the case of Experiment 1 or 2, even when the pressing means for pressing the blood collecting bag was replaced with another means as shown in FIGS. 4 to 10, respectively, the similar results were obtained.

In this connection, as the method of discharging each of the separated components without removing the blood collecting bag from the centrifugal container, it may be possible to use only the sucking method as described above which sucks the supernatant plasma layer through a tube connected to the upper end portion of the blood collecting bag and discharge it, without using the pressing means.

However, it has been found that the above-mentioned method is not appropriate due to the following reasons. That is to say, where the above-mentioned method is adopted alone, the inner pressure of the blood collecting bag is reduced into a vacuum pressure. For this reason, when the plasma layer is being discharged with the advance of pump suction, the two opposing inner surfaces of the bag are brought into contact with each other in particular at the upper portion of the bag. In addition, since gaps (channels) are produced between the inner surfaces of the bag so as to extend from the upper end discharge port 5 (outlet) of the bag to the vicinity of the fused edge portions of the bag, the separated component lower than the plasma layer, in particular the lowermost erythrocyte layer is sucked upwardly along the produced gaps. As a result, the erythrocyte is likely to be mixed with the plasma, thus causing another problem in that the yield for plasma collection is lowered.

Further, when the lower bully coat layer 1s required to be collected after the plasma layer has been collected, the quantity of liquid within the blood collecting bag is further reduced, so that the two opposing inner surfaces of the bag are brought into further tight contact with each other. Therefore, a great quantity of erythrocyte is likely to be discharged through the gaps formed between the inner surfaces of the bag. In other words, the collection of the buffy coat layer must be stopped before the erythrocyte is mixed. This means that a quantity of the buffy coat layer remains within the blood collecting bag. As a result, it is difficult to separate the bully coat layer from the erythrocyte layer effectively.

In contrast with this, if the suction motion for the separated component by the sucking means is taken place in addition to the pressing motion for the blood collecting bag 1, the two opposing inner surfaces of the bag are not brought into contact with each other at the upper portion of the bag and further any channel is not be produced between the opposite two sheets, so that it becomes possible to transfer and collect the separated component with high yield.

As described above, in the separated component transferring apparatus and method according to the present invention, it is possible to improve the yield for the blood component obtained by the centrifugal separation, and further to reduce the time and labor required for separation.

Finally, it should be noted that the present invention is no limited to the above mentioned embodiment. The scope of the invention is defined only by the following claims.

What is claimed is:

1. An apparatus for transferring a separated component in a liquid contained in a flexible bag in airtight condition after centrifuging the flexible bag, which comprises:

a centrifugal container for accommodating the flexible bag therein, said container being adapted to be removably attached to a centrifugal separator, and said centrifugal container having a soft material part formed in at least one portion thereof;

pressing means for pressing said flexible bag accommodated in said centrifugal container to increase an inner pressure of said flexible bag while said flexible bag is released from an airtight condition, so that a predetermined separated component can be discharged from the bag, said pressing means being operated under the condition that said centrifugal container is removed from the centrifugal separator, wherein said pressing means comprise at least one pushing member for pushing the soft material part of said centrifugal container in such a manner that the soft material part is deformed inwardly to project inside said centrifugal container, and driving means for driving said pushing member; and wherein said centrifugal container includes an annular frame portion and a cylindrical portion coupled to said frame portion, and said cylindrical portion constitutes said soft material part of said centrifugal container.

2. The apparatus as claimed in claim 1, wherein said pressing means includes a pair of push members which push the soft material part of said centrifugal container from opposite directions.

3. The apparatus as claimed in claim 2, wherein at least one of said push member is movable by said driving means.

4. The apparatus as claimed in claim 1, wherein each of said push members includes a roller for pushing the soft material part of said centrifugal container.

5. The apparatus as claimed in claim 1, further comprising sucking means for sucking the separated component in the flexible bag.

6. The apparatus as claimed in claim 5, wherein the apparatus further comprises a container for receiving the separated component, wherein said sucking means includes means for reducing the pressure of an atmosphere in which said separated component receiving container is put.

7. A method of transferring a separated component in a liquid contained in a flexible bag under airtight condition, which comprises the steps of:

accommodating the flexible bag in which the liquid is contained under airtight condition into a centrifugal container which is to be removable attached to a centrifugal separator, said centrifugal container having a soft material part formed in at least one portion thereof;

centrifuging the flexible bag accommodated in said centrifugal container using the centrifugal separator to separate the liquid in the flexible bag into the components thereof;

removing said centrifugal container from the centrifugal separator together with the flexible bag put therein and then fixing the centrifugal container to a fixing means;

pressing the soft material part of said centrifugal container under the condition that the flexible bag is put in said centrifugal container to increase inner pressure of said flexible bag while releasing the airtight condition thereof, to take out a predetermined component in the liquid which has been separated by the centrifugation outside said flexible bag; and wherein said centrifugal container includes an annular frame portion and a cylindrical portion coupled to said frame portion, and said cylindrical portion constitutes said soft material part of said centrifugal container.

8. The method as claimed in claim 7, further comprising the step of sucking the separated component in the flexible bag by reducing the pressure of an atmosphere in which a separated component receiving container is put, while pressing the flexible bag.

* * * * *

UNITED STATES PATENT AND TRADEMARK OFFICE
CERTIFICATE OF CORRECTION

PATENT NO. : 5,632,906
DATED : May 27, 1997
INVENTOR(S) : Noboru ISHIDA et al

It is certified that error appears in the above-indentified patent and that said Letters Patent is hereby corrected as shown below:

In Column 9, line 33, delete "be".
In Column 9, line 34, delete "happened" and insert -- happen --.
In Column 10, line 27, delete "bully" and insert -- buffy --.
In Column 10, line 44, delete "bully" and insert -- buffy --.
In Column 10, line 52, delete "bully" and insert -- buffy --.
In Column 10, line 61, delete "bully" and insert -- buffy --.
In Column 10, line 63, delete "bully" and insert -- buffy --.
In Column 16, line 47, delete "bully" and insert -- buffy --.
In Column 18, line 25, delete "bully" and insert -- buffy --.
In Column 18, line 36, delete "bully" and insert -- buffy --.

Signed and Sealed this

Seventh Day of October, 1997

Attest:

BRUCE LEHMAN

Attesting Officer

Commissioner of Patents and Trademarks